United States Patent [19]

Smith, Jr.

[11] Patent Number: 4,551,567

[45] Date of Patent: Nov. 5, 1985

[54] DEETHERIFICATION PROCESS

[75] Inventor: Lawrence A. Smith, Jr., Bellaire, Tex.

[73] Assignee: Chemical Research & Licensing Company, South Houston, Tex.

[21] Appl. No.: 648,071

[22] Filed: Sep. 7, 1984

Related U.S. Application Data

[63] Continuation-in-part of Ser. No. 517,220, Jul. 25, 1983.

[51] Int. Cl.$^4$ .................... C07C 29/00; C07C 31/04
[52] U.S. Cl. .................................... 568/907; 568/698; 568/899; 585/639
[58] Field of Search .................. 568/907; 585/639

[56] References Cited

U.S. PATENT DOCUMENTS

| | | | |
|---|---|---|---|
| 2,519,061 | 8/1950 | Mason | 568/907 |
| 2,544,392 | 3/1951 | Moore et al. | 568/907 |
| 2,736,743 | 2/1956 | Schmidle et al. | 568/907 |
| 2,888,490 | 5/1959 | Walter et al. | 568/907 |
| 3,121,124 | 2/1964 | Verdol | 568/907 |
| 3,170,000 | 2/1965 | Verdol | 568/907 |
| 4,287,379 | 9/1981 | Brunner et al. | 568/907 |
| 4,320,232 | 3/1982 | Volkamer et al. | 568/907 |
| 4,405,822 | 9/1983 | Bezman | 568/907 |
| 4,409,421 | 10/1983 | Herwig et al. | 568/907 |

Primary Examiner—J. E. Evans
Attorney, Agent, or Firm—Kenneth H. Johnson

[57] ABSTRACT

Ethers such as isobutyl tertiary butyl ether are dissociated into their component alcohols and isolefins by heat stabilized catalyst compositions prepared from nuclear sulfonic acid, for example, macroporous crosslinked polyvinyl aromatic compounds containing sulfonic acid groups are neutralized with a metal of Al, Fe, Zn, Cu, Ni, ions or mixtures and alkali, alkaline earth metals or ammonium ions by contacting the resin containing the sulfonic acid with aqueous solutions of the metals salts and alkali, alkaline earth metal or ammonium salts. The catalysts have at least 50% of the sulfonic acid groups neutralized with metal ions and the balance of the sulfonic acid groups neutralized with alkali, alkaline earth ions or ammonium ions.

18 Claims, No Drawings

DEETHERIFICATION PROCESS

This invention was made with Government support under Contract No. DE-FC07-80CS40454 awarded by the Department of Energy. The Government has certain rights in this invention.

This application is a continuation in part of Ser. No. 517,220 filed July 25, 1983.

BACKGROUND OF THE INVENTION

1. Field of the Invention

The present invention relates to acid cation exchange resins which have been modified to form substantially neutral metal salts thereof, which have been found to be superior catalysts for several processes.

2. Related Art

The acid cation exchange resins are well known and have a wide variety of uses. The resins are cation exchangers, which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150 degrees C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is generally used in a granular size of about 0.25 to 1 mm, although particles from 0.15 mm up to about 2 mm may be employed. The finer catalysts provide high surface area, but also result in high pressure drops through the reactor. The macroreticular form of these catalysts have much larger surface area exposed and limited swelling which all of these resins undergo in a non-aqueous hydrocarbon medium compared to the gelular catalysts.

The acid cation exchange resins have been widely used in etherifications and have recently been found to be useful for deetherifications and transetherifications. Other reactions known to be carried out with the aid of cation exchange resins include dimerizations, hydration of olefins, esterifications and epoxidations.

The modified cation exchange resin catalyst of the present invention have been found particularly useful for deetherifications, dehydration and hydration of organic compounds.

The modified catalysts of the present invention exhibit substantial improvement in thermal stability compared to the base resin, however, the catalysts continue to exhibit the properties of acid catalysts. Furthermore, the present catalysts have been observed to be more selective in reactions.

The simplicity and safety of the present process which produces the present high temperature, active resin type catalysts is an advantage over other types of stabilizations wherein the resins are chlorinated or brominated.

SUMMARY OF THE INVENTION

In its broader aspects the present invention relates to improved catalysts compositions which are nuclear sulfonic acid solid resins which have at least 50% of the sulfonic acid groups neutralized with metal ions of Group 4b, 5b, 6b, 7b, 8, 1b or 2b, and of the Periodic Table of elements, the rare earth metals or mixtures thereof, and the balance of the sulfonic acid groups neutralized with an alkali metal or alkaline earth metal, ammonium or mixtures thereof. The sulfonic acid may be attached to any polymeric backbone. The preferred metals are Ti, V, Cr, Mn, Fe, Co, Ni, Cu, Zn, Zr, Nb, Mo, Ru, Rh, Pd, Ag, Cd, Ta, W, Re, Pl, Ce, Nd, Sm, and Eu.

The present invention includes the method of preparing cation resin catalysts, cation resin catalysts, and the processes using the catalysts.

In a preferred embodiment the present catalyst is prepared by contacting a macroporous matrix containing a sulfonic acid group with aqueous solution of metal salts and solutions of alkali metal salts, alkaline earth metal salts and/or ammonium salts to neutralize the acid groups. Alkali metal and alkaline earth metal ions are preferred for the neutralization.

In a preferred procedure the present catalysts are prepared by contacting a sulfonic acid cation exchange resin comprising a macroporous matrix of a polyvinyl aromatic compound crosslinked with a divinyl compound and having thereon from about 3 to 5 milli equivalents of sulfonic acid groups per gram of dry resin (1) with an aqueous solution of a soluble compound of an alkali metal or alkaline earth metal of Group 1a or 2a of the Periodic Table of elements or mixtures thereof in an amount to neutralize all of the available sulfonic acid groups and (2) thereafter contacting said neutralized resin with an aqueous solution of a soluble salt of a metal as described and preferably a soluble salt of Al, Fe, Zn, Cu, Ni or mixtures thereof to replace at least 50% of the alkali metal, alkali earth metal or mixtures thereof associated with said sulfonic acid groups with said metal.

In an alternate procedure the present cation resin catalyst composition is prepared by contacting, a sulfonic acid cation exchange resin comprising a macroporous matrix of a polyvinyl aromatic compound crosslinked with a divinyl compound and having thereon from about 3 to 5 milli equivalents of sulfonic acid groups per gram of dry resin, (1) with an aqueous solution of a soluble metal salt as described and preferably of Al, Fe, Zn, Cu, Ni or mixtures thereof to neutralize at least 50% to less than 100% of the available sulfonic acid groups with said metal ions to produce a partially neutralized resin and (2) thereafter contacting said partially neutralized resin with an aqueous solution containing a soluble compound of an alkali or alkaline earth metal of Group 1a or 2a, of the Periodic Table of elements or mixture thereof to neutralize the remaining sulfonic acid groups.

Following either procedure substantially equivalent catalysts which are fully neutralized are obtained.

The resin catalyst composition is a solid comprising a macroporous matrix of polyvinyl aromatic compound crosslinked with a divinyl compound and having thereon from about 3 to 5 milli equivalents of sulfonic acid groups per gram of dry resin, wherein at least 50% to less than 100% preferably at least 59% and more preferably 70 to 90% of said sulfonic acid groups are neutralized with a metal ion as described and preferably Al, Fe, Zn, Cu, Ni or mixtures thereof and said sulfonic acid groups not neutralized with said metal ion are neutralized preferably with alkali or alkaline earth metal ions of Group 1a or 2a of the Periodic Table of elements, ammonium ions or mixtures thereof.

The modified acidic cation exchange resins, i.e., the neutralized resins of the present invention have been found to be stable at fairly high temperatures (for resin type catalysts), e.g., temperatures of 150°-200° C. may be used for operations with good time trend for catalyst activity and structural integrity. The catalyst are suitable for both liquid phase and vapor phase (or mixed phase) organic reactions.

The catalysts are preferably employed in a fixed bed, in any of the conventional configurations, such as tubular reactors, packed in a single continuous bed or in supported structures as described in U.S. Pat. Nos. 4,250,052; 4,215,011 and 4,302,356.

The catalyst may be used in processes by passing the reactants in vapor phase or liquid phase (as indicated by equilibrium considerations) through the fixed bed. Similarly, the catalyst in supported structures as described in U.S. Pat. Nos. 4,250,052; 4,215,011 and 4,302,356 may be used as both a catalyst contact and distillation structure where the reaction products are conveniently concurrently made and separated by distillation.

The deetherification to produce an olefin and an alcohol is most conveniently carried out in a fixed bed with the feed in vapor phase at temperature in the range of 150° C–190° C. preferably below 180° C., i.e., about 160° C. to 170° C., at LHSV (liquid hourly space velocity) preferably of about 1 to 10 and more preferably about 3 to 6. The ethers which may be easily dissociated are those of the general formula

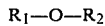

R$_1$—O—R$_2$ wherein R$_1$ is a hydrocarbon radical having 4 or 5 carbon atoms and R$_2$ is a hydrocarbon radical having 1 to 6 carbon atoms. The hydrocarbon radicals may be straight chain or branches. Some illustrative ethers are methyl tertiary butyl ether, ethyl tertiary butyl ether, propyl tertiary butyl ether, butyl tertiary butyl ether, tertiary butyl tertiary butyl ether, pentyl tertiary butyl ether, hexyl tertiary butyl ether, methyl 2-methyl butyl ether, methyl 3-methyl butyl ether, ethyl n-amyl ether, methyl isoamyl ether and the like.

The dissociation of the ethers is favored at higher temperatures, that is, the equilibrium constant shifts toward dissociation at the higher temperatures recited. It is an advantage that the higher temperature allow higher pressures of 4 to 40 atmospheres, preferably about 5 to 10 atmospheres of operation in the vapor phase and the hydrocarbon, i.e., C$_4$ or C$_5$ olefin, dissociation product can be condensed at the higher pressure without refrigeration, i.e., condensation water at ambient temperatures can be used.

The use of the present catalyst rather than conventional acidic cation exchange resins for deetherification is advantageous since the reaction is more selective to the production of the olefin at high conversions. In addition, the present catalysts substantially eliminate the formation of ether by-products and acetals.

Dehydration of alcohols such as tertiary butyl alcohol can also be carried out at high temperatures and pressure in vapor phase, e.g., 130° C.–150° C. at LHSV in the range 1 to 10 using the present catalyst in a fixed bed usually with pressure drops through the bed of about 1 to 30 psig, preferably about 5 to 15 psig.

Hydration of unsaturated hydrocarbons such as tertiary butene to form alcohols is preferably carried out in liquid phase at temperatures in the range of 100° C. to 130° C. at LHSV in the range of 1 to 10 using the present catalyst in a fixed bed with sufficient pressure to maintain the liquid phase.

DETAILED DESCRIPTION OF THE INVENTION

Any of the acidic cation exchange resins known to the art and described above, preferably the macroporous form may be employed in the present modification procedure, however, polystyrene crosslinked with divinyl benzene is preferred. The macroporous resins are frequently referred to as macroreticular. This type of resin structure has been described in the art since the early 1960's, for example, by K. A. Kun, and R. Kunin, "J. Poly Sci", A-1 Vol 6, page 264 (1968) and R. Kunin, E. Meitzner, N. Bortnick, "J. Am. Chem. Soc.", Vol. 84, page 305 (1962) and U.S. Pat. No. 3,037,052 to Bortnick.

The macroporous resins have heterogenous structures, and consist of agglomerates of very small gelular microspheres. Each microsphere has a microporous matrix structure identical to that of common gelular resins but much smaller than the gelular resin beads. Thus, the macroporous resins are formed of areas of microporous gel matrix interspersed with macropores. A common example of this material is Rohm and Haas Amberlyst 15. Those macroreticular sulfonic acid cation exchange resins having a specific pore volume of at least about 0.01 cc./gm. and preferably in excess of 0.03 cc./gm. are suitable for the present invention.

These matrixes (matrices) are sulfonated as described earlier in order to introduce sulfonic acid groups (—SO$_3$H) into the matrix to form strongly acidic catalysts. It should be noted that anion forms of the resins are also known and prepared by the introduction of amine groups into the matrix. Hence, generally acidic or basic catalyst are known and used.

The catalysts of the present invention are substantially neutral (although all of the sulfonic acid sites are neutralized, on hydrolysis the present catalyst will exhibit a slightly acidic pH) having been neutralized with specific metal ions and preferably alkali and/or alkaline earth metal ions to obtain specific catalytic properties.

As described earlier a nuclear sulfonic acid resin, for example, macroreticular resin catalyst, preferably polyvinyl styrene crosslinked with divinyl benzene and sulfonated to contain from 3 to 5 milli equivalents of sulfonic acid is contacted with a solution of a water soluble salts, as described and in a one embodiment, a salt of Al, Fe, Zn, Cu, Ni or mixtures thereof and a salt of an alkali or alkaline earth metal. Soluble salts of the metals described are known, but some examples are aluminum chloride, iron (Fe+3) chloride, nickel chloride, copper (Cu+2) chloride, zinc chloride, copper (Cu+2) sulfate, iron (Fe+3) sulfate, zinc sulfate, and the like. The mixtures of metal ions may include any two or more of the metals disclosed.

Preferred alkali and alkaline earth metals are Li, Na, K, Mg, Ca, Sr, Ba, or mixtures thereof. The mixtures of alkali metal ions or alkaline earth metal ions may comprise any two or more of the elements from Periodic Table group 1a and 2a. Suitable soluble salts include sodium chloride, potassium chloride, lithium sulfide, magnesium acetate, calcium bromide, strontium bromide, barium bromide and the like. Ammonium chloride, for example, is illustrative of the soluble salts suitable for use in the present process Preferred Procedure The preferred method of catalyst preparation is advantageous since it is the metal ion which is the active species and it is simpler to replace the alkali or alkaline ion (or ammonium ion) to the desired extent than avoid removing the metal ion in the alternate procedure. The neutralization of the sulfonic acid sites with the alkali or alkaline earth metal salt solution (or ammonium salt) can be easily and quickly carried out using a brine, e.g., NaCl in a saturated solution.

The displacement of alkali, alkaline earth or ammonium ions with the metal ion may be controlled by using the metal salt solution in portions containing metal ion in theoretical amounts to displace the alkali, alkaline or ammonium ions in stages or in a single solution of a theoretical amount. Analysis of a portion of the catalyst can readily determine if the desired displacement has taken place and if not, further treatment and analysis can be carried to arrive at the desired level of metal ion concentration in the catalyst.

Of course, a continuous stream contact of a specific concentration of the metal salt can be plotted for specific rates, temperature, and the like and an accurate and reproduced synthesis established.

The solutions are normally at ambient room temperature and atmospheric pressure, although temperatures in the range of 10° C. to 80° C., are suitable and both suband super atmosphere pressure could be used for both procedures.

As a final step in both disclosed processes the catalyst is preferably washed with a water substantially free of electrolytes, i.e., deionized water or distilled water, to remove any residual contact solution. The catalyst may be dried in air or in various known driers or washed with methanol then heated. In some utilizations the catalyst may be loaded in the reactor wet and dried as part of the start up process.

Alternate Procedure

The amount of soluble metal salt present is that amount which will react with (neutralize) at least 50% of the active sulfonic acid sites present in the resin being contacted and preferably an excess of salt is present. In no event will there be a 100% neutralization of the sulfonic active sites with metal ions even if an excess of the salt beyond 100% is present, since these salts form acidic solutions, and an equilibrium is established, depending on the acidity, between the hydrogen ion on the sulfonic acid group and the metal ion. It can be expected that one $Fe^{+3}$ ion will neutralize three sulfonic acid sites as will the aluminum ion, whereas metals of +2 valence will neutralize two sites per ion.

Hence, after the contact with the metal salt solution, there will still be some active sulfonic acid sites. These residual sulfonic acid sites are neutralized by contacting the resin with a solution of an alkali or alkaline earth metal salt or ammonium salt. These solutions will neutralize the residual sulfonic acid sites, such that the final resin product is a fully neutralized material, or in practice very weakly acidic.

In the final alkali neutralization step under the alternate procedure, care must be exercised not to contact the partially neutralized resin with a large excess of alkali or alkaline earth metal ions, (a slight excess up to about 20% may be used, beyond that required to neutralize the residual sulfonic acid groups) since they appear to form double salts or possibly elute the metal ions, which may reduce the catalytic activity of the catalyst. An empirical technique of the manner to produce highly active fully neutralized resins is the use of ordinary tap water which is slightly alkaline, e.g. pH 8, which normally contains dissolved alkali and alkaline earth salts. Generally an amount over about 10 ml of such tap water per ml of partially neutralized catalyst would be excessive.

The minimum amount of the alkali, alkaline earth or ammonium salt is dependent on the extent of neutralization in the first step. For example, a salt solution of copper sulfate has a high pH (3.5) and obtained a high degree of copper ion exchange, hence only 3 ml of tap water wash per ml of resin produced an excellent catalyst, whereas 10 ml of tap water wash per ml of resin would be excessive for this catalyst. For an iron sulfate solution, pH 1, the ion exchange equilibrium is lower and a 10 ml tap water wash is reasonable.

Because different metal salts (first stage neutralization) have different pH's and the ion exchange equilibrium is affected by pH, some experimentation will be desirable, initially with the amount of alkali, alkaline earth or ammonium salt solution to determine acceptable wash amounts. However, once having determined equilibrium constants for each solution, the amount necessary can be calculated such that an excess may be readily avoided.

It should also be appreciated that the catalytic activity varies for the different metal ions and the activity of one metal ion modifier in one process may not be similar when the catalyst is used in a different process. In regard to deetherification, it has been observed that the activity of the catalyst increases $Ni < Zn < Cu < Fe$ and Al.

The modification of the acidic cation exchange resins according to the present invention as noted above, substantially changes the characteristic of the resins, namely, the high temperature properties are substantially improved and the activity of the catalyst is changed. One particular benefit of the change of activity in regard to deetherification is the greater selectivity of the deetherified product to the olefin corresponding to the ether, for example, deetherification of methyl tertiary butyl ether using an unmodified resin produces small but detectable amounts of isobutane, dimethyl ether and acetal, whereas the modified catalysts substantially reduce these side reactions.

The deetherifcation process using the present catalyst is carried out in vapor phase, since the dissociation is favored by higher temperatures and vapor phase (less molecular contact for the reverse reaction).

Temperatures up to about 200° C. may be used, but temperatures up to 160° C. to 170° C. are preferred. Pressure may range from atmospheric up to the pressure at which the reactants and products are reduced to the liquid phase. Generally, as a desirable expedient the system is operated at a pressure at which the desired olefin product is condensed with the least cooling, e.g., in MTBE dissociation, isobutene can be condensed with available ambient temperature cooling water at 70-100 psig, preferably 80-90 psig.

The etherification reaction is known to be reversible. The reaction is reversible (deetherification or dissociation) in the liquid phase, mixed liquid and vapor phase (the catalytic distillation) and in vapor phase; however, it has been observed that the dissociation equilibrium concentrations appear to be about three times more favorable towards producing isobutene (or isoamylene) in the vapor phase as compared to a liquid phase system.

The present dissociation is preferably carried out in vapor phase, at a temperature which will maintain the reactants in the vapor phase. The dissociation is endothermic.

The preparation of the ether from isobutene or isoamylene and its subsequent dissociation according to the present process is not redundant as it may at first appear. Isobutene is a component of C$_4$ refinery streams. The separation of the isobutene from such streams in a pure state by fractionation, because of the closeness of the component boiling points, is extremely difficult even more so if extremely high purity isobutene is desired. However, the isobutene is readily and selectively reacted with C$_1$-C$_6$ alcohols to form the ethers which can be separated from the other C$_4$ components by conventional distillation. Thus, when the ethers are dissociated according to the present invention extremely high purity isobutene is produced, that is isobutene with very little of any other C$_4$ present. The same considerations apply to the isoamylene.

The alkyl tertiary butyl ether or alkyl tertiary amyl ether, preferably C$_1$ to C$_6$ alkyl tertiary butyl ether or C$_1$ to C$_6$ alkyl tertiary amyl ether, may be produced by any of the methods known in the art and should itself be a relatively pure feed to the present dissociation, quite obviously, preferably at least 97 wt % ether and more preferably at least about 99 wt % ether.

The neutralized cation exchange resin is preferably employed in a fixed bed. A fluidized or moving bed would operate; however, the attrition of the catalyst particles would render such a system unrealistic and at the least undesirable. A catalyst packing system and catalyst structures as described in U.S. Pat. No. 4,215,011 may be used in the present dissociation and provides a convenient means of handling the catalyst packing. However, in the strictly vapor phase system, since the dissociation is in the vapor phase and not in a distillation mode, the openness of these structures is not required and the resin beads packed into a rector provide adequate open space to pass the vapor through without inordinately high pressure drops.

In the vapor phase system it is convenient to pack or load the catalyst, which is usually in granular or bead form, into a heat exchanger having means to introduce heat thereto in order to maintain the vapor phase and desired temperatures. The feed to dissociation reactor is preferably a down flow, so as not to fluidize the catalyst bed which would result in attrition of the catalyst. In the event that the catalyst does become fouled with heavy byproducts, these may be removed by washing the catalyst with the liquid feed. The fixed bed may be located in a tubular reactor wherein tubes of $\frac{1}{2}$ to 2 inches diameter are positioned through a shell into which a heat exchange medium, e.g., steam, may be emitted to maintain the heat of reaction.

The most readily available alkyl tertiary butyl ether is methyl tertiary butyl ether (MTBE), which is widely used as an octane improver for gasoline; however, for the specialized purpose of the present invention other alcohols can be produced in the processes used to etherify isobutene or isoamylene, i.e., C$_1$ to C$_6$ alcohols can be used as taught in commonly assigned application U.S. Pat. No. 4,336,407, which is incorporated herein in its entirety. These alternative ethers may have other uses but the benefit that some offer to the present process justifies their manufacture. The alcohols derived from the dissociation of the present ethers are monohydric, e.g., methanol, ethanol, isopropanol, tertiary butanol, isobutanol and the like.

The C$_3$ and higher alcohols produced by dissociation of 3-6 carbon atom alkyl tertiary ethers do not azeotrope with isobutene or isoamylene. For example, by using normal propyl tertiary butyl ether in the process, the alcohol dissociation product, N-propyl alcohol does not form an azeotrope with isobutene dissociation product and is easily separated therefrom in a fractionation.

The separation of methanol (product from MTBE) from isobutene is not difficult and may be readily obtained by water washing of the dissociation product. The wash water, however, should be further treated for recycle and the methanol recovered, if the process is to be economically operated.

The temperature in the dissociation reactor is at or above the vaporization temperature of the ether (e.g., MTBE) at the pressure of the reactor. The pressure in the reactor can be subatmospheric up to a pressure where the boiling point of the ether is up to about 200° C., generally about 10 to 300 psig at LHSV of 2 to 10. The temperature in the dissociation reactor is determined by the desired rate of dissociation of the ether, (i.e., higher temperature favors dissociation) and by the decomposition temperature of the catalyst. With these points in view the normal operating temperature is in the range of 50° C. to 200° C.

The dissociation of the specified alkyl tertiary butyl ether to form isobutene and alcohol is an equilibrium reaction according to the following equation:

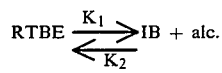

The rate constants K$_1$ and K$_2$ are both temperature dependent, however, the dissociation reaction (RTBE−K$_1$ IB+alc.) increases much more rapidly with temperature rise than does the reverse reaction IB+alc−K$_2$ RTBE). The same is true for the alkyl tertiary amyl ether also.

Thus, the temperatures within the ranges specified elsewhere herein are preferred.

The hydration of olefins, particularly, tertiary olefins, such as isobutene or isoamylene is carried in liquid phase at lower temperature, e.g., around 100° C. to 130° C. and sufficient pressure to maintain the liquid phase.

The dehydration of alcohols, particularly tertiary alcohols such as tertiary butanol (TBA) is carried out either in vapor phase or liquid phase (vapor phase is preferred because lower pressure may be used) at temperature of 130° C. to 150° C. Very high conversion is obtained at relatively good space rates (LHSV 1 to 10).

The following examples will illustrate the invention but are not intended to limit the scope thereof.

EXAMPLES 1-8

In the following examples, example 1 is a control. The catalyst is ordinary Amberlyst 15 purchased from Rohm and Haas. The modified catalyst are the same Amberlyst 15 treated with the various salt solutions and water as indicated. Each catalyst was dried prior to use by washing with methanol and heating. Each catalyst was placed in the same reactor and the same feed was fed through under the same conditions.

The reactor was a bench scale tubular reactor (⅜" OD copper tubing) containing 60 ml of the dry catalyst and heated with a steam jacket. The column was positioned vertically and a stainless steel mesh screen used to support the catalyst bed. The feed to each run was a 50/50 isobutanol/isobutyl tertiary butyl ether stream. The temperature was held at 150° C.–160° C. for examples 2–8 and 100° C. for example 1. The LHSV was between 3.5–5 for each run and pressure was 65–90 psig bed exit pressure.

Each of the metal salt solutions used in the first stage treatment were 20% concentration. The metal salt solution was contacted with the resin at ambient room temperature (about 25° C.). After the contact with the metal salt each sample was washed with deionized water then as indicated in TABLE I the sample was washed with tap water and in some cases with deionized water. A final pH, which is the pH of the final wash water through the catalyst is reported. This pH reflects the pH of the modified resin at the time.

In TABLE I the treatment steps and solutions are set out followed by the results of the deetherification run. TABLE II is a typical analysis of the tap water used to neutralize the remaining sulfonic acid groups.

EXAMPLE 9

The catalyst of example 6 was used for a dehydration of tertiary butyl alcohol at 140° C., LHSV 3. The conversion of TBA to isobutene was 90 mole %.

EXAMPLE 10

Using the same catalyst as example 9, the temperature was lowered to 125° C. and water and isobutene fed through the catalyst bed in liquid phase (325 psig) at LHSV 3. The isobutene comprised 15% of a $C_4$ stream. Five % of isobutene was converted to TBA.

EXAMPLE 11

Using the same catalyst and reactor as example 4 methanol was dehydrated to produce dimethyl ether. The reactor was heated with high pressur steam (43 lbs. pressure) through the jacket. The conditions and results are reported in TABLE III.

EXAMPLE 12

A catalyst was prepared by contacting macroreticular sulfonated resin (Amberlyst 15) with a 20% solution of NaCl until the acid sites were neutralized by washing three volumes of resin three times with two volumes of the 20% NaCl each time (total six volumes of NaCl). Following this the resin was washed twice with one-half volume deionized water. The neutralized catalyst was then washed three times with two volumes of a 20% solution of zinc sulfate (total six volumes). Following this the resin was washed twice with one-half volume of deionized water. Analysis of the final catalyst showed 7.6 wt. % Zn and 2.6 wt % Na.

Sixty ml. of this catalyst was dried with methanol and placed in the reactor described in the prior examples. A feed of 99.9+% MTBE was passed (downflow) through the catalyst with a jacket temperature of 371° F. (160 pound steam) at LHSV of 3–4. Average conversion of MTBE was 91.6 wt. %. The selectivity to isobutene was 99.9 wt % and selectivity to methanol was 99.7 wt % (GC). The MTBE was fed as a liquid to the reactor and vaporized in the reactor. The back pressure on the reactor was 80 psig.

TABLE I

| EXAMPLE | 1 | 2** | 3 | 4*** | 5 | 6 | 7 | 8 |
|---|---|---|---|---|---|---|---|---|
| Modification | | | | | | | | |
| Metal Salt Modifier | None | FeCl2 | Fe2(SO4)3 | FeCl3 | CuSO4 | Fe(SO4)3ZnSO4 | | NiCl2 |
| pH, Modifier Solution | — | 1 | 1 | 1 | 3.5 | 1 | 4.5 | 5.1 |
| Tap Water Wash | | | | | | | | |
| pH | — | 8 | 8 | 8 | 8 | 8 | 8 | 8 |
| liters | — | not rec | app 6 | app 30 | 0.3 | 3 | 1.2 | 1.0 |
| Deionized Water Wash, l. | — | not rec | 0 | 0 | 1.3 | 2 | 1.0 | 5.0 |
| pH of Final Wash | — | 4.5 | 3.7 | 6.6 | 6.1 | 4.3 | 6.4 | 6.4 |
| Deetherification | | | | | | | | |
| Conversion of IBTBE, mole % | 53* | 85 | 88 | 14 | 88 | 94 | 49 | 14 |
| Selectivity to Isobutene, mole % | 97.5 | 98.1 | 97.3 | 99.3 | 97.0 | 95.5 | 99.0 | 98.8 |

*100° C. to avoid catalyst decomposition
**Analysis of modified catalyst showed 6.18 wt % iron, chloride 70 ppm
***Analysis of modified catalyst showed 5.83 wt % iron, chloride 80 ppm

TABLE II

| Arsenic | 0.01 mg. per liter |
|---|---|
| Barium | 0.50 " |
| Chromium | 0.02 " |
| Copper | 0.02 " |
| Iron | 0.02 " |
| Lead | 0.02 " |
| Manganese | 0.02 " |
| Selenium | 0.0002 " |
| Silver | 0.01 " |
| Zinc | 0.02 " |
| PORTABLE WATER ANALYSIS | |

TABLE II-continued

| | | |
|---|---|---|
| Calcium | 5 | mg. per liter |
| Magnesium | 1 | " |
| Sodium | 230 | " |
| Carbonate | 11 | " |
| Bicarbonate | 432 | " |
| Sulfate | 3 | " |
| Chloride | 83 | " |
| Flouride | 2.3 | " |
| Nitrate as in CaCO3 | 0.01 | " |
| Dissolved Solids | 547 | " |
| Alkalinity as in CaCO3 | 003 | " |
| pH | 8.7 | " |

TABLE III

| Hours on Stream | 1 | 1.8 | 2.4 | 2.9 |
|---|---|---|---|---|
| Reactor Temp. (Steam Temp °F.) | 290* | 338** | 338 | 338 |
| LHSV | 6 | 6 | 2.5 | 2.5 |
| Reaction Pressure, psig | 160 | 200 | 200 | 200 |
| Product Analysis Wt. % | | | | |
| Methanol | 98.7 | 94.7 | 81.5 | 79.7 |
| DME | 1.3 | 5.3 | 18.5 | 20.3 |
| Water | | Not seen by GC | | |

*Stem at 43 pounds pressure
**Steam at 100 pounds pressure

The invention claimed is:

1. A process for the deetherification of ethers comprising of contacting said ether in vapor phase with a solid catalyst composition comprising a resin of a macroporous matrix of polyvinyl aromatic compound crosslinked with a divinyl compound and having thereon from about 3 to 5 milli equivalents of sulfonic acid groups per gram of dry resin, wherein at least 50% to less than 100% of said sulfonic acid groups are neutralized with a metal of Al, Fe, Zn, Cu, Ni or mixtures thereof and said sulfonic acid groups not neutralized with said metal ion are neutralized with alkali metal ions or alkaline earth metal ions of Group 1a or 2a of the Periodic Table of elements or mixtures thereof.

2. The process according to claim 1 wherein said alkali metal ions or alkali earth metal ions are Li, Na, K, Mg, Ca, Sr, Ba or mixtures thereof.

3. The process according to claim 2 wherein said alkali metal ions or alkaline earth metal ions are Na, K, Mg, Ca or mixtures thereof.

4. The process according to claim 1 wherein said macroporous matrix is polyvinyl styrene crosslinked with divinyl benzene.

5. The process according to claim 4 wherein said metal ion is Al.

6. The process according to claim 4 wherein said metal ion is Fe.

7. The process according to claim 4 wherein said metal ion is Zn.

8. The process according to claim 4 wherein the metal ion is Cu.

9. The process according to claim 4 wherein the metal ion is Ni.

10. The process according to claim 1 wherein at least 59% of said sulfonic acid groups are neutralized with said metal ions.

11. The process according to claim 1 wherein from 70 to 90% of said sulfonic acid groups are neutralized with said metal ions.

12. The process composition according to claim 1 wherein the metal is a mixture of two or more of Al, Fe, Zn, Cu or Ni.

13. The process according to claim 1 wherein the ether is methyl tertiary butyl ether.

14. The process according to claim 1 wherein the ether is isobutyl tertiary butyl ether.

15. The process according to claim 1 wherein the temperature of said contacting is at a temperature up to about 200° C.

16. The process according to claim 15 wherein the temperature is up to 170° C.

17. The process according to claim 1 wherein the ether is a $C_1$ to $C_6$ alkyl tertiary butyl ether.

18. The process according to claim 1 wherein the ether is a $C_1$ to $C_6$ alkyl tertiary amyl ether.

* * * * *